(12) United States Patent
Boersma et al.

(10) Patent No.: US 10,598,163 B2
(45) Date of Patent: Mar. 24, 2020

(54) SEMI-FREE ROTATING CRANKSHAFT ACTUATOR TO PRE-STRESS AND FAST RELEASE A SPRING LOADABLE PLUNGER FOR AN ORAL HEALTHCARE APPLIANCE

(71) Applicant: KONINKLIJKE PHILIPS N.V., Eindhoven (NL)

(72) Inventors: Joldert Maria Boersma, Zuidhorn (NL); Pieter Herman Klokman, Ureterp (NL); Klaas Kooijker, Drachten (NL); Egbert Van De Veen, Ijsselmuiden (NL); Aaldert Geert Zijlstra, Zuidlaren (NL); Stephanus Jacob Gerardus Tamminga, Groningen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 98 days.

(21) Appl. No.: 15/780,269

(22) PCT Filed: Nov. 30, 2016

(86) PCT No.: PCT/IB2016/057195
§ 371 (c)(1),
(2) Date: May 31, 2018

(87) PCT Pub. No.: WO2017/098371
PCT Pub. Date: Jun. 15, 2017

(65) Prior Publication Data
US 2018/0363635 A1 Dec. 20, 2018

Related U.S. Application Data

(60) Provisional application No. 62/264,388, filed on Dec. 8, 2015.

(51) Int. Cl.
*F04B 9/04* (2006.01)
*A61C 17/028* (2006.01)
(Continued)

(52) U.S. Cl.
CPC .............. *F04B 9/04* (2013.01); *A61C 17/028* (2013.01); *A61C 17/225* (2013.01); *F04B 9/06* (2013.01);
(Continued)

(58) Field of Classification Search
CPC ... F04B 9/04; F04B 9/06; F16H 21/24; A61C 1/0092
See application file for complete search history.

(56) References Cited

U.S. PATENT DOCUMENTS 2,717,597 A 9/1955 Hein, Jr.
2,797,488 A 3/1974 Hurschman
(Continued)

FOREIGN PATENT DOCUMENTS

CN 201692079 U 1/2011
CN 204192778 U 3/2015
(Continued)

*Primary Examiner* — Michael Leslie

(57) ABSTRACT

A semi-free rotating crankshaft actuator (80) for an oral healthcare appliance comprises a chamber (82), a spring loadable plunger (85), and a crank mechanism (88). The crank mechanism (88) comprises at least a drive pin (90) rotatably driven about a drive axis (96), and a crank shaft (94) semi-freely rotatable about the drive axis, wherein the crank shaft (94) couples to the spring loadable plunger (85) and is partially driven about the drive axis (96) via (i) the drive pin (90) in a first operational mode, (ii) the spring loadable plunger (85) in a second operational mode, and (iii) the drive pin (90) in a third operational mode that comprises at least completing an incomplete actuation of the plunger (84) from an undesired end position to the desired end position in response to the crank shaft (94) pushing the
(Continued)

plunger (84) from the undesired end position to the desired end position.

15 Claims, 8 Drawing Sheets

(51) Int. Cl.
*A61C 17/22* (2006.01)
*F04B 9/06* (2006.01)
*F04B 19/22* (2006.01)
*F04B 23/02* (2006.01)
*F16H 21/24* (2006.01)

(52) U.S. Cl.
CPC .............. *F04B 19/22* (2013.01); *F04B 23/02* (2013.01); *F16H 21/24* (2013.01)

(56) References Cited

U.S. PATENT DOCUMENTS

| | | | |
|---|---|---|---|
| 4,527,463 A * | 7/1985 | Albarda | F04B 9/06 92/84 |
| 8,753,117 B2 * | 6/2014 | Edwards | A61C 1/0092 239/359 |
| 9,255,571 B2 * | 2/2016 | Wang | F04B 9/06 |
| 10,299,884 B2 * | 5/2019 | Kloster | A61C 1/0092 |
| 2010/0324485 A1 | 12/2010 | Cowe | |

FOREIGN PATENT DOCUMENTS

| | | |
|---|---|---|
| EP | 1051984 A2 | 11/2000 |
| GB | 662425 | 12/1951 |
| WO | 2013190428 A1 | 12/2013 |
| WO | 2014140979 A1 | 9/2014 |

* cited by examiner

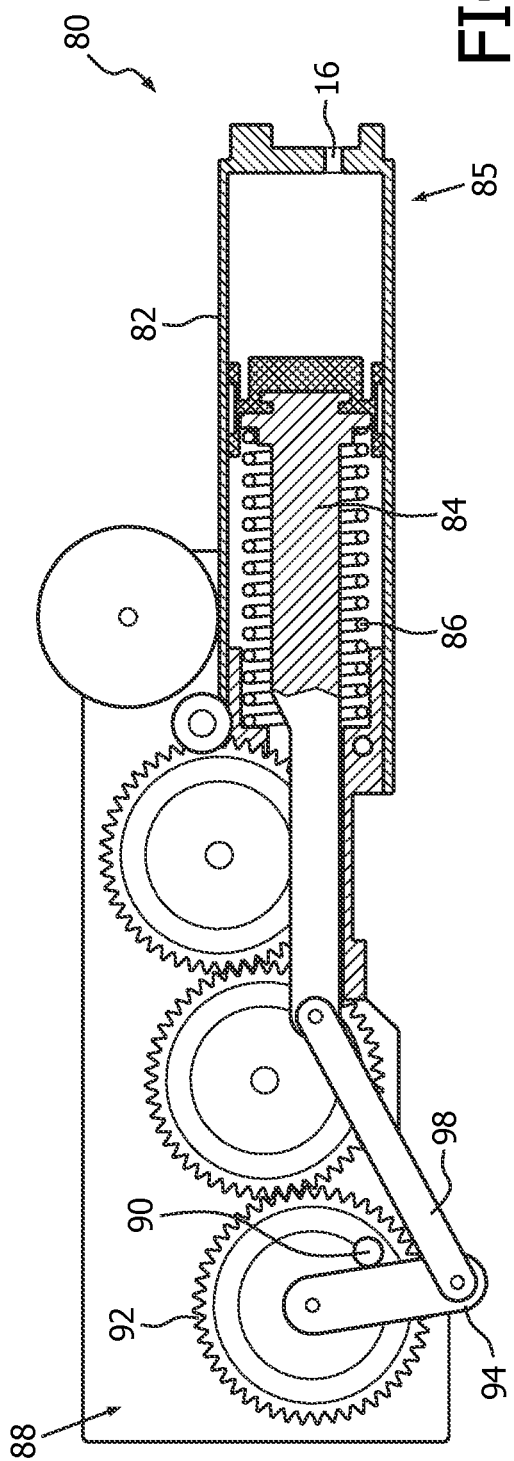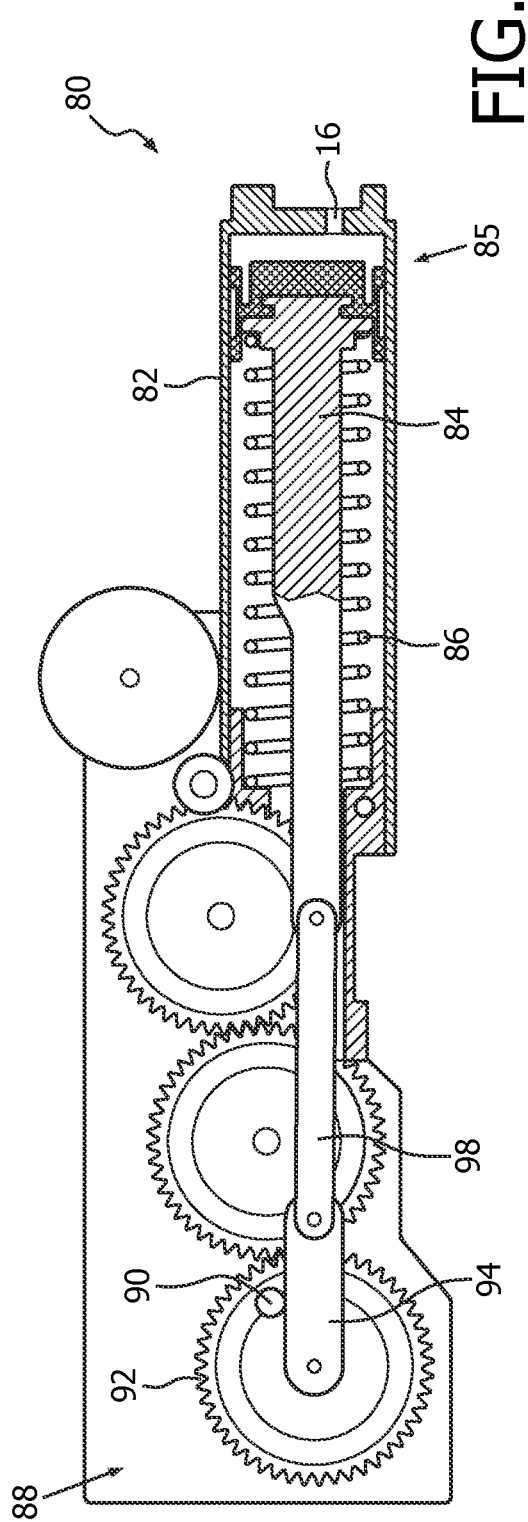

SEMI-FREE ROTATING CRANKSHAFT ACTUATOR TO PRE-STRESS AND FAST RELEASE A SPRING LOADABLE PLUNGER FOR AN ORAL HEALTHCARE APPLIANCE

CROSS-REFERENCE TO PRIOR APPLICATIONS

This application is the U.S. National Phase application under 35 U.S.C. § 371 of International Application No. PCT/IB2016/057195, filed on Nov. 30, 2016 which claims the benefit of U.S. Provisional Patent Application No. 62/264,388, filed on Dec. 8, 2015. These applications are hereby incorporated by reference herein.

The present embodiments relate generally to oral healthcare appliances and more particularly, to a semi-free rotating crankshaft actuator to pre-stress and fast release a spring loadable plunger for an oral healthcare appliance and a method thereof.

With oral healthcare, one generally thinks of simply brushing one's teeth. However, brushing of one's teeth, alone, does not clean interdental areas of the teeth very well. Accordingly, dentists recommend flossing in addition to brushing. To improve interdental cleaning, several devices are on the market that can be used at home. One such device, the Airfloss™ device, creates a combination of water droplets and air that is accelerated through a nozzle for a high impact velocity. The air is compressed in a cylinder by a piston that it moved forward by a compressed spring.

In a prior art version of the device, a motor drives a pinion gear that has a limited number of teeth along part of its circumferential area and interacts with a rack gear that is part of the piston. The rotation of the pinion gear, forces the rack gear in a backwards direction which results in compression of the spring. Once the pinion has rotated so far that no teeth are interacting with the rack gear anymore, the piston is forced forward by the spring. However, this type of device has limitations on the ability to reset the mechanism for repeated operations, and the mechanism can experience mechanical difficulties if operated in too fast a manner.

Accordingly, an improved method and apparatus for overcoming the problems in the art is desired.

In accordance with one aspect, an actuator drive train mechanism comprises a crank mechanism which is freely rotatable around a driving axis. The crank mechanism is coupled to its revolving axis if the crank speed is lower than the speed of the driving axis. In the embodiments disclosed herein, the crank mechanism is used to pretension a spring loadable plunger, prior to releasing the plunger at its maximum spring stress.

In accordance with another aspect, one embodiment comprises a drive train mechanism that includes a crank-rod drive mechanism that can pull back a spring loadable plunger and subsequently release it freely. In case something prevents the piston from moving fully forward, the drive train mechanism will ensure that the piston is completely forced forward before pulling it back. The drive train mechanism advantageously solves a locking issue that has been found for the prior known drive trains as discussed herein.

According to one embodiment, a semi-free rotating crankshaft actuator for an oral healthcare appliance comprises a chamber, a spring loadable plunger, and a crank mechanism. The chamber includes a principal axis, an interior surface with a spring compression stop at a proximal end thereof, and at least one inlet and at least one outlet at a distal end thereof. The spring loadable plunger is operable within the chamber along the principal axis between a tensioned position near the proximal end of the chamber and a released position near the distal end of the chamber. The spring loadable plunger comprises (i) a plunger having a distal end thereof configured for traversing the interior surface of the chamber along the principal axis in a fluid tight relationship and (ii) a spring, positioned over a proximal end of the plunger and positioned between the compression stop and the distal end of the plunger. The spring has at least two compression states including a first compression state (i.e., a tensioned state) greater than a second compression state (i.e., a released state), wherein responsive to the spring being unloaded from the first compression state to the second compression state, the spring actuates the plunger at a first velocity from the tensioned position to the released position. The released position comprises (a) a desired end position within the chamber in response to a first actuator condition and (b) an undesired end position within the chamber, different from the desired end position, in response to a second actuator condition, different from the first actuator condition. The crank mechanism couples to the spring loadable plunger for cycling the spring loadable plunger between the tensioned and released positions.

The crank mechanism comprises at least a drive pin rotatably driven about a drive axis, and a crank shaft semi-freely rotatable about the drive axis. The crank shaft couples to the spring loadable plunger and is partially driven about the drive axis via (i) the drive pin in a first operational mode that comprises loading the spring into the first compression state in response to the crank shaft pulling the plunger from the desired end position to the tensioned position, (ii) the spring loadable plunger in a second operational mode that comprises actuating the plunger from the tensioned position to the released position in response to the spring being unloaded from the first compression state to the second compression state, and (iii) the drive pin in a third operational mode that comprises the crank shaft pushing the plunger from the undesired end position. For example, the third operational mode includes at least one of (a) completing an incomplete actuation of the plunger from the undesired end position to the desired end position and (b) moving the plunger from the undesired end position (e.g., in case the plunger comes to rest beyond the desired end position, but before the tensioned position) in response to the crank shaft pushing the plunger from the undesired end position.

According to another embodiment of the semi-free rotating crankshaft actuator, the first actuator condition comprises the released spring loadable plunger overcoming friction within the chamber and any obstruction of the at least one outlet, and the second actuator condition comprises the released spring loadable plunger incompletely overcoming friction within the chamber and/or any obstruction of the at least one outlet. In another embodiment, the first velocity comprises a velocity sufficient for developing at least a minimum required pressure within the chamber for expelling, via the at least one outlet, a desired quantity of air and/or liquid, and/or mixture of air and liquid. Air and/or liquid can be input into the chamber, for example, via the at least one inlet.

In yet another embodiment, the first operational mode further comprises the plunger being initially located at the desired end position within the chamber and the drive pin engaging the crank shaft for exerting a pushing force on the crank shaft, causing the crank shaft coupled to the spring loadable plunger to move the spring loadable plunger at a second velocity from the released position to the tensioned position, the second velocity being less than the first velocity. In a further embodiment, the second velocity comprises a velocity sufficient for maintaining a desired duty cycle for loading and unloading of the spring, further for inputting and subsequently expelling a desired quantity of air and/or liquid, and/or mixture of air and liquid, for example, via the at least one inlet and the at least one outlet, respectively.

In yet another embodiment, the second operational mode further comprises the plunger being initially located at the tensioned position within the chamber and the drive pin losing engagement with the crank shaft in response to the spring of the spring loadable plunger (a) actuating the plunger at the first velocity from the tensioned position to the released position and (b) exerting a pulling force on the crank shaft. In addition, the third operational mode further comprises the plunger initially coming to rest at the undesired end position within the chamber prior to reaching the desired end position and the drive pin engaging the crank shaft for exerting a pushing force on the crank shaft, causing the crank shaft coupled to the spring loadable plunger to move the spring loadable plunger at the second velocity from the undesired end position to the desired end position, and then further on to the tensioned position.

In one embodiment of the semi-free rotating crankshaft actuator, the crank mechanism further comprises a connection member coupled between the crank shaft and the spring loadable plunger. In addition, a first end of the connection member is rotatably coupled to a distal end of the crank shaft and a second end of the connection member is rotatably coupled to a proximal end of the plunger. In another embodiment, the chamber further comprises a cylindrical chamber. In addition, the at least one inlet comprises a one-way inlet valve and the at least one outlet comprises a one-way outlet valve.

In yet another embodiment, the semi-free rotating crankshaft actuator includes wherein the drive pin rotatably driven about the drive axis comprises a circular drive gear having a principal surface, the drive pin further being extended perpendicular from the principal surface and located on the circular drive gear at a given radial distance from the drive axis. In a further embodiment, the drive pin rotatably driven about the drive axis comprises a drive lever crank having a principal surface, the drive pin further being extended perpendicular from the principal surface and located on the drive lever crank at a given distance from the drive axis. In a still further embodiment, the drive pin rotatably driven about the drive axis comprises a driven circular drive gear having a principal surface, a one-way clutch (e.g., using a spring wrapped tightly around an axis) having a first end thereof affixed to a pin that extends perpendicular from the principal surface located on the circular drive gear at a given radial distance from the drive axis, and wherein a second end of the one-way clutch is configured for one-directional driving engagement with the crank shaft.

In another embodiment, an oral healthcare appliance, comprises the semi-free rotating crankshaft actuator, wherein the at least one outlet is configured for receiving a nozzle having a guidance tip; a motor operable for driving the drive axis; at least one reservoir for receiving at least one of a liquid and a gas; a fluid pump assembly for delivering at least one of a liquid and a gas from the at least one reservoir to the at least one inlet of the chamber; and a controller for controlling (i) an operation of the motor and (ii) a delivery of liquid and/or gas via the fluid pump assembly to the at least one inlet according to at least one requirement of a given procedure of the oral healthcare appliance for expelling a desired quantity and/or mixture of gas and/or liquid at a given rate and duty cycle via the nozzle.

In still another embodiment, a method of providing semi-free rotating crankshaft actuation for an oral healthcare appliance, comprises providing a chamber having a principal axis, an interior surface with a spring compression stop at a proximal end thereof, and at least one inlet and at least one outlet at a distal end thereof. The method further comprises operating a spring loadable plunger within the chamber along the principal axis between a tensioned position near the proximal end of the chamber and a released position near the distal end of the chamber. The spring loadable plunger comprises (i) a plunger having a distal end thereof configured for traversing the interior surface of the chamber along the principal axis in a fluid tight relationship and (ii) a spring, positioned over a proximal end of the plunger and positioned between the compression stop and the distal end of the plunger, having at least two compression states including a first compression state greater than a second compression state. Responsive to the spring being unloaded from the first compression state to the second compression state, the spring actuates the plunger at a first velocity from the tensioned position to the released position. The released position comprises (a) a desired end position within the chamber in response to a first actuator condition and (b) an undesired end position within the chamber, different from the desired end position, in response to a second actuator condition, different from the first actuator condition.

The method further comprises cycling, via a crank mechanism, the spring loadable plunger between the tensioned and released positions. The crank mechanism comprises at least a drive pin rotatably driven about a drive axis, and a crank shaft semi-freely rotatable about the drive axis. The crank shaft couples to the spring loadable plunger and is partially driven about the drive axis via (i) the drive pin in a first operational mode that comprises loading the spring into the first compression state in response to the crank shaft pulling the plunger from the desired end position to the tensioned position, (ii) the spring loadable plunger in a second operational mode that comprises actuating the plunger from the tensioned position to the released position in response to the spring being unloaded from the first compression state to the second compression state, and (iii) the drive pin in a third operational mode that comprises the crank shaft pushing the plunger from the undesired end position. For example, the third operational mode includes at least one of (a) completing an incomplete actuation of the plunger from the undesired end position to the desired end position and (b) moving the plunger (84) from the undesired end position (e.g., in case the plunger comes to rest beyond the desired end position, but before the tensioned position) to the tensioned position in response to the crank shaft pushing the plunger from the undesired end position.

In a further embodiment, the method includes wherein the first actuator condition comprises the released spring loadable plunger overcoming friction within the chamber and any obstruction of the at least one outlet, and wherein the second actuator condition comprises the released spring loadable plunger incompletely overcoming friction within the chamber and/or any obstruction of the at least one outlet. In addition, the method includes wherein the first velocity comprises a velocity sufficient for developing at least a minimum required pressure within the chamber for expelling, via the at least one outlet, a desired quantity of air and/or liquid, and/or mixture of air and liquid.

According to yet another embodiment, the first operational mode further comprises the plunger being initially located at the desired end position within the chamber and the drive pin engaging the crank shaft for exerting a pushing force on the crank shaft, causing the crank shaft coupled to the spring loadable plunger to move the spring loadable plunger at a second velocity from the released position to the tensioned position, the second velocity being less than the first velocity. The second operational mode further comprises the plunger being initially located at the tensioned position within the chamber and the drive pin losing engagement with the crank shaft in response to the spring of the spring loadable plunger (a) actuating the plunger at the first velocity from the tensioned position to the released position and (b) exerting a pulling force on the crank shaft. In addition, the third operational mode further comprises the plunger initially coming to rest at the undesired end position within the chamber prior to reaching the desired end position and the drive pin engaging the crank shaft for exerting a pushing force on the crank shaft, causing the crank shaft coupled to the spring loadable plunger to move the spring loadable plunger at the second velocity from the undesired end position to the desired end position, and then further on to the tensioned position. Furthermore, the second velocity comprises a velocity sufficient for maintaining a desired duty cycle for loading and unloading of the spring, further for inputting and subsequently expelling a desired quantity of air and/or liquid, and/or mixture of air and liquid.

Advantages and benefits will become apparent to those of ordinary skill in the art upon reading and understanding the following detailed description.

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

FIG. 1 a perspective view of an oral healthcare appliance, in the form of an oral irrigator device, according to an embodiment of the present disclosure FIG. 2 a partial cut-away side view showing various components of the known actuator drive train of a prior art appliance;

FIGS. 3A, 3B, and 3C are schematic diagram views illustrating components of a semi-free rotating crankshaft actuator to pre-stress and fast release a spring loadable plunger for an oral healthcare appliance according to an embodiment of the present disclosure shown in various stages of intended drive train operation;

FIG. 4 is a schematic diagram view illustrating an example of an intended drive train operation of the semi-free rotating crankshaft actuator configured for overcoming an abnormal or unintended condition of the drive train plunger during operation of the actuator of FIG. 3, the abnormal or unintended condition arising in response to a force, acting on the plunger against the spring direction, which can vary, for example, due to friction of the plunger seal and/or an obstruction of the output nozzle and/or other causes;

FIG. 5 is a cut-away perspective view taken along the principal axis of an actuator according to one embodiment of the present disclosure;

FIG. 6 is a close-up cut-away perspective view taken along the principal axis of the actuator according to one embodiment of the present disclosure;

Figure 7:
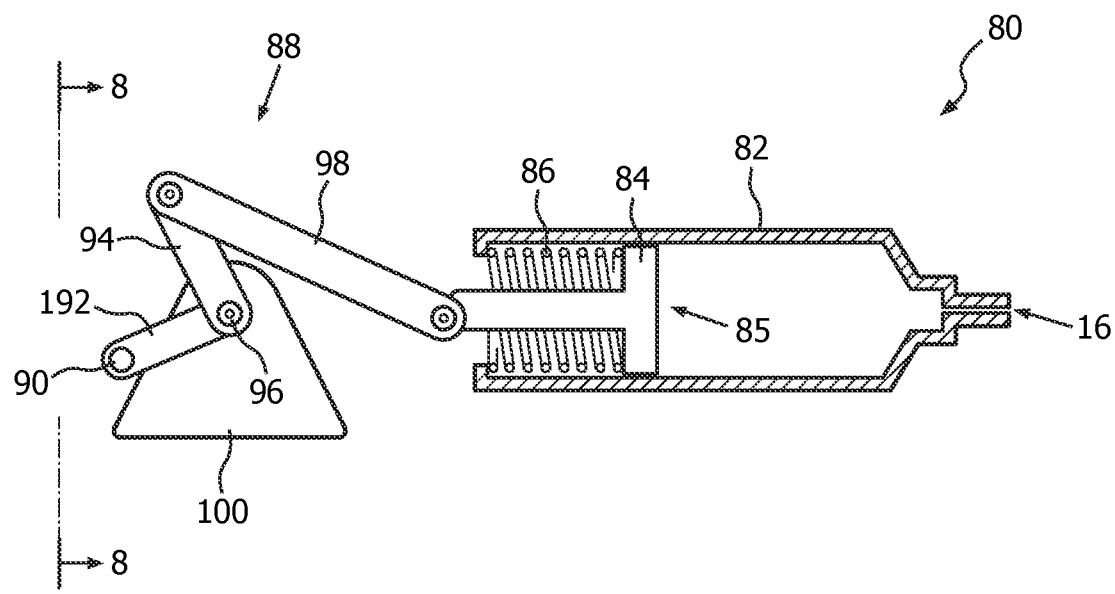
FIG. 7 is a schematic diagram view illustrating various components of a semi-free rotating crankshaft actuator to pre-stress and fast release a spring loadable plunger for an oral healthcare appliance according to another embodiment of the present disclosure.
Figure 9A:
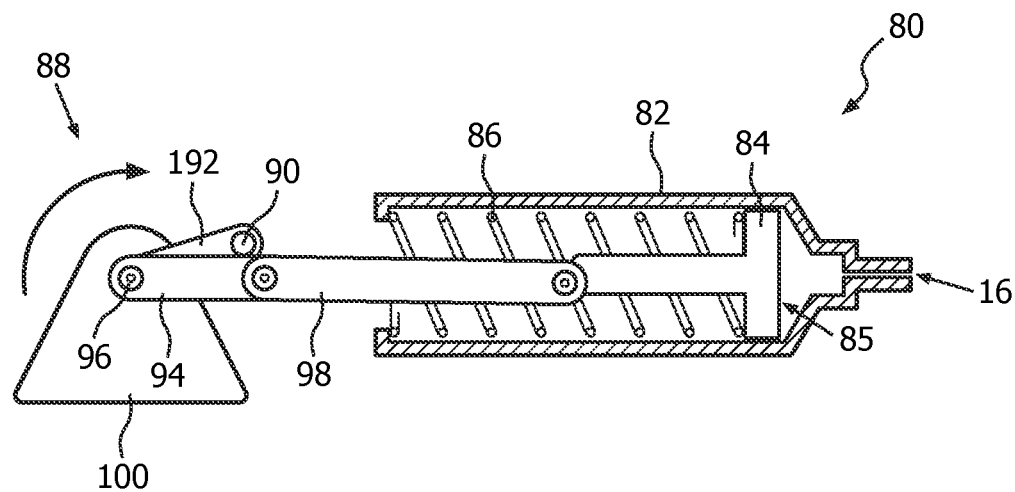
Figure 9B:
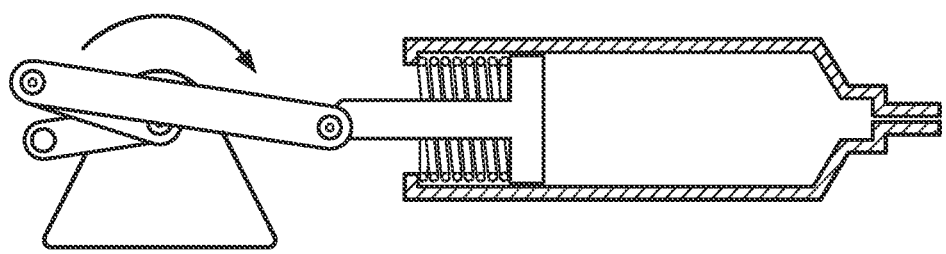
Figure 9C:
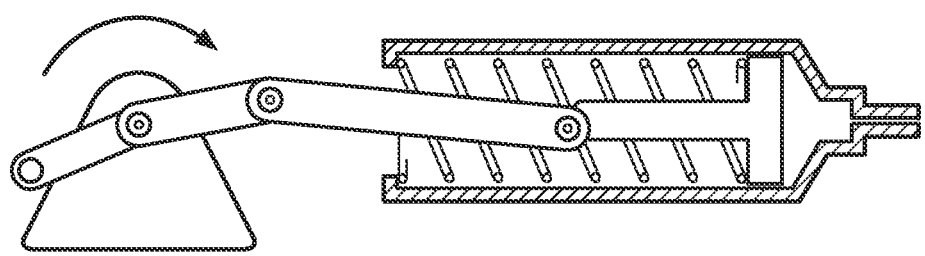
Figure 10:
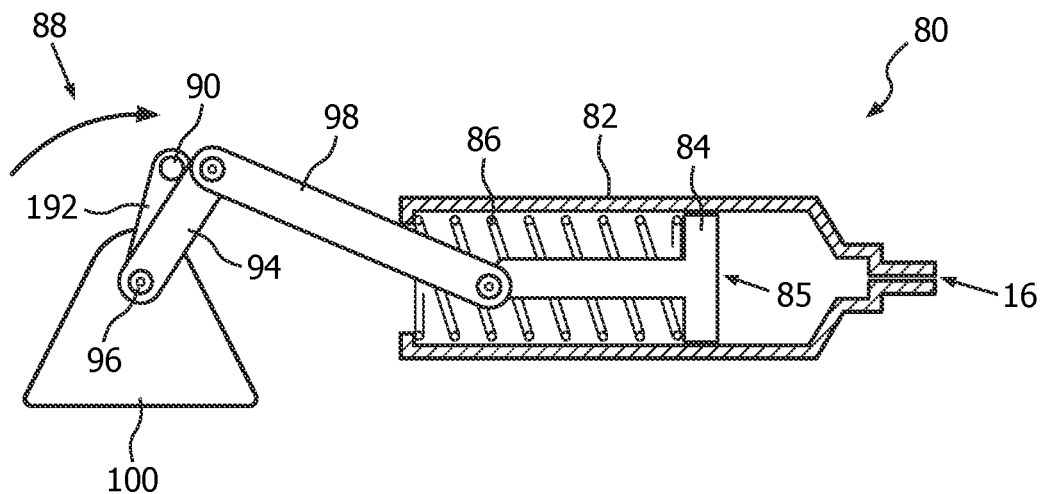
Figure 11:
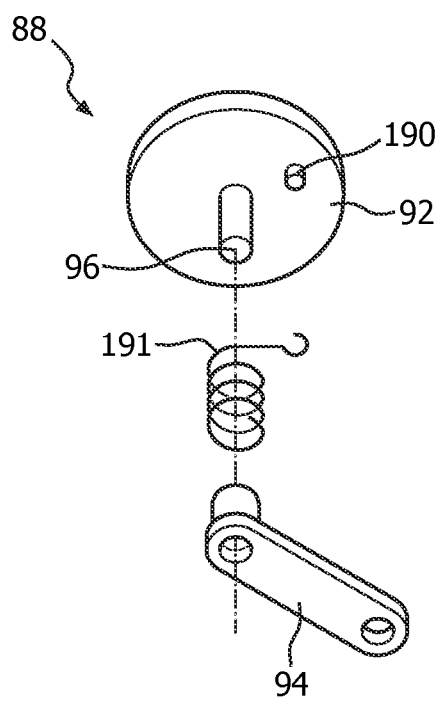
Figure 12:
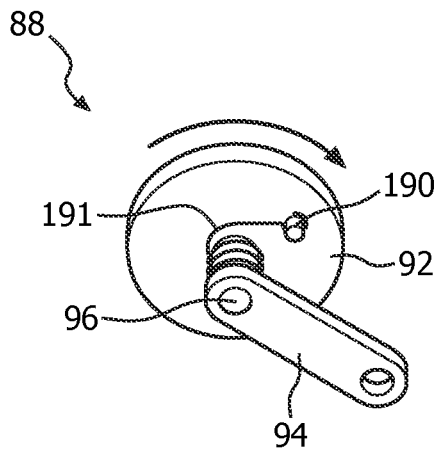

FIGS. 9A, 9B, and 9C are schematic diagram views illustrating various stages of intended drive train operation of the semi-free rotating crankshaft actuator for an oral healthcare appliance of FIG. 7;

FIG. 10 is a schematic diagram view illustrating an example of an intended drive train operation of the semi-free rotating crankshaft actuator configured for overcoming an abnormal or unintended condition of the drive train plunger during operation of the actuator of FIGS. 9A-9C, the abnormal or unintended condition arising in response to a force, acting on the plunger against the spring direction, which can vary, for example, due to friction of the plunger seal and/or an obstruction of the output nozzle and/or other causes;

FIG. 11 is an exploded schematic view of a crank mechanism that comprises a drive pin and crankshaft arrangement of a semi-free rotating crankshaft actuator for an oral healthcare appliance according to another embodiment of the present disclosure; and FIG. 12 is a schematic view of the crank mechanism for the semi-free rotating crankshaft actuator of FIG. 11 according to an embodiment of the present disclosure.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

Figure 1:
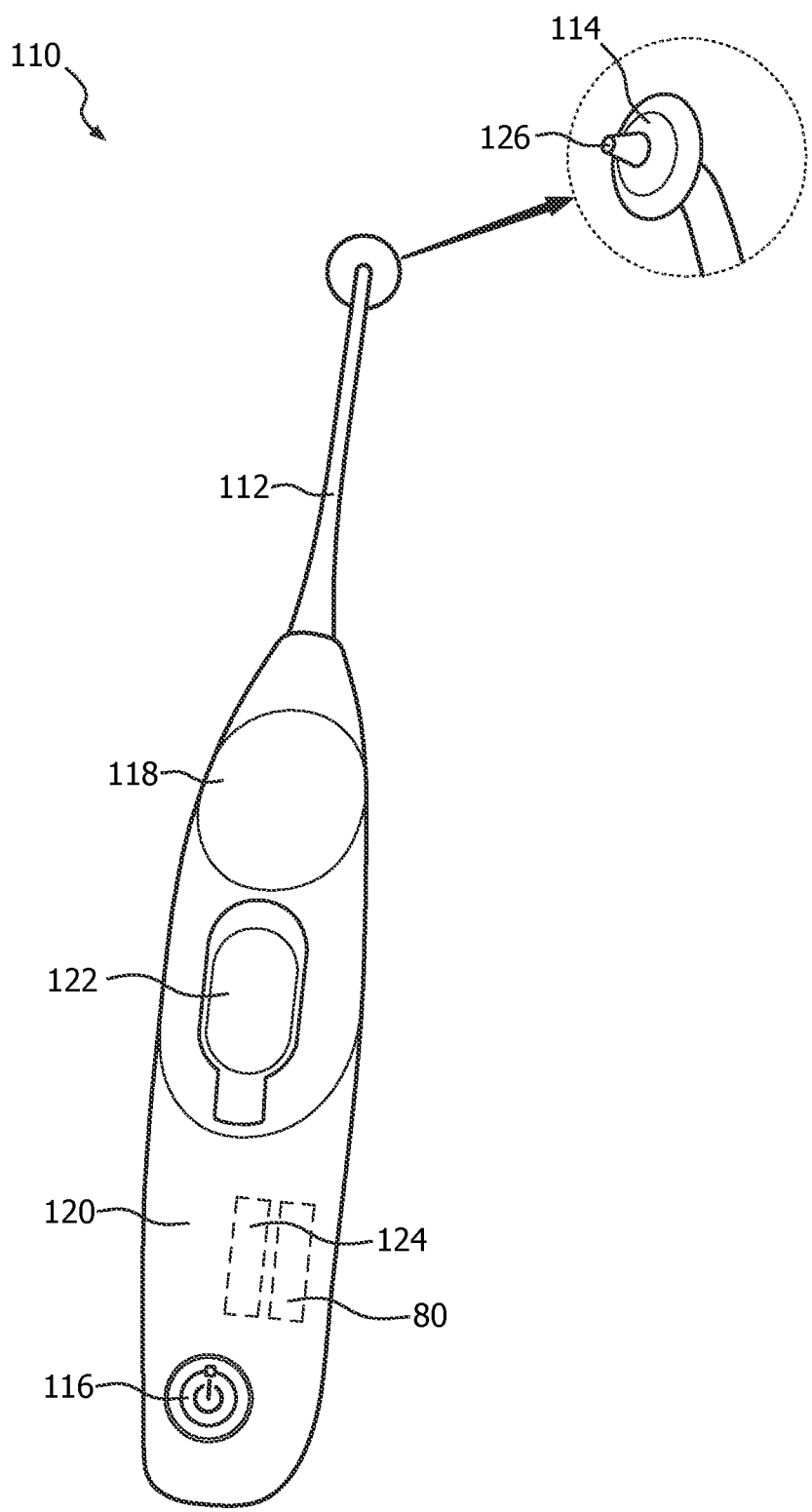

Turning now to FIG. 1, a perspective view is shown of an oral healthcare appliance 110, in the form of an oral irrigator device, according to an embodiment of the present disclosure. The oral irrigator device 110 includes a nozzle 112 with a guidance tip 114. The oral irrigator device 110 includes a power ON/OFF button 116, an activation button 118, an ergonomic handle 120, at least one liquid reservoir 122, a microburst pump that comprises a semi-free rotating crankshaft actuator 80 as discussed herein, and control electronics 124.

In operation, when the device 110 is turned on by means of the ON/OFF button 116, pressing the activation button 118 causes the pump 80 to be operable as discussed herein, further for pumping fluid from the reservoir 122 to an orifice 126 of the guidance tip 114 of nozzle 112 in the form of liquid droplets. Control electronics 124 (or controller) can further comprise one or more of modules for carrying out one or more modes of operation of the semi-free rotating crankshaft actuator 80 in conjunction with the oral irrigator device 110.

Figure 2:
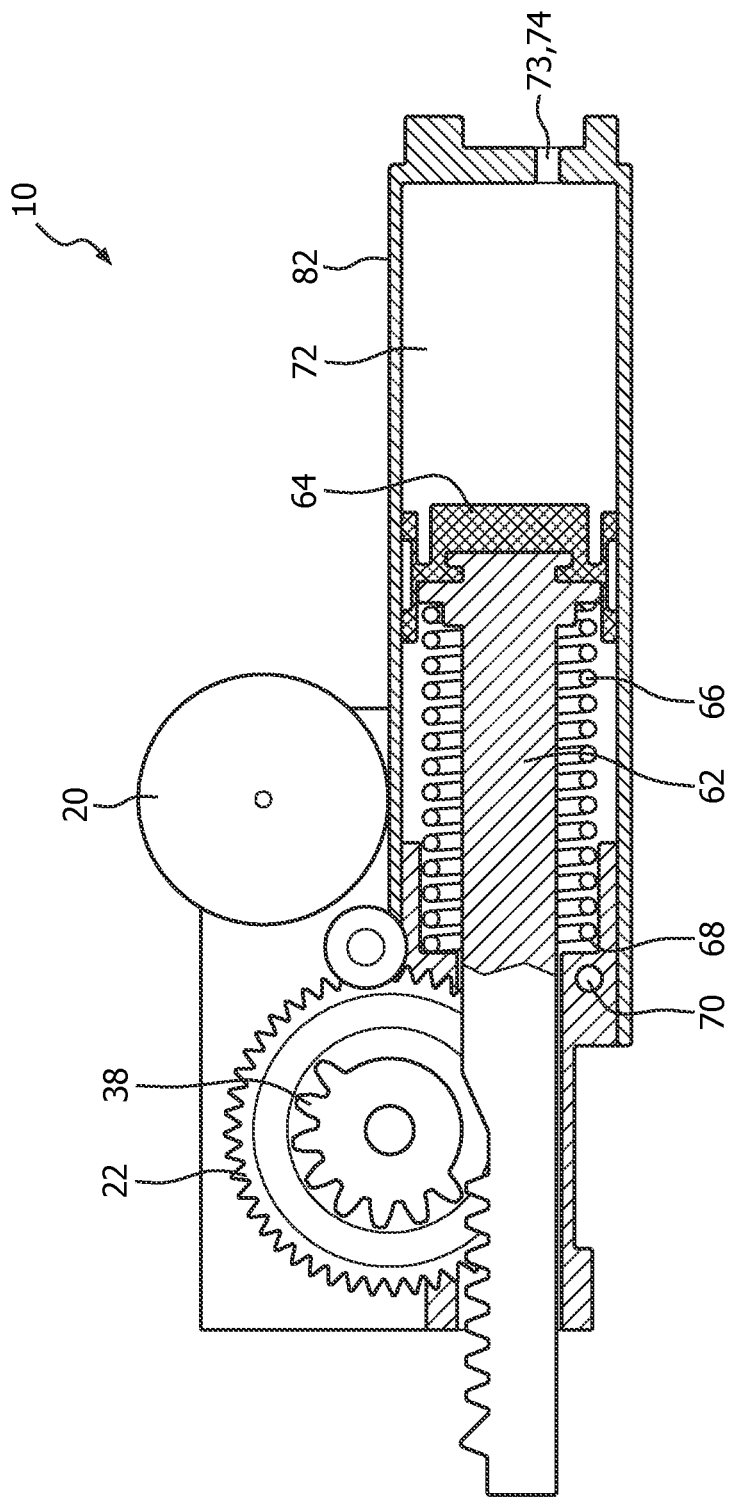

Reference will now be made with respect to FIG. 2, which illustrates a partial cut-away side view of a rack and pinion drive mechanism 10 of the known prior art device. The apparatus includes a motor 20 configured for providing a high torque, Motor 20 includes an output shaft (not shown) on which is mounted a motor drive gear 22. The motor drive gear engages a compound pinion gear 38, which has two parts, (i) a first part comprising a set of teeth around approximately one-half of the circumference of the thereof and (ii) a second part which has no teeth. The pinion gear 38 mates with a linear rack member 62 which is positioned within proximal end of gas cylinder 12. Rack member 62 includes a set of spaced teeth on the upper surface thereof. The distal end of rack member 62 includes a seal member or plunger 64 which mates in a fluid tight relationship with the interior surface of gas cylinder 12. Extending from the distal end of rack 62 at plunger 64 and encircling the rack along most of the length thereon is a compression spring 66. The proximal end 68 of spring 66 is positioned against a stop element 70 located within a body portion of cylinder 12.

The configuration shown in FIG. 2 is representative of a condition of the device when the spring 66 is compressed, and air is drawn into cylinder 12 by the plunger 64 that it moved backwards by the rack gear 62. In further operation, responsive to the pinion gear 38 rotating so far that no teeth are interacting anymore with the rack gear 62, plunger 64 is pushed in a forward direction (i.e., to the right-side of the figure) by the spring 66, driving the air 72 in the cylinder 12 out through a one-way inlet/outlet valve 73, 74 where the air is mixed with water, to form droplets, which are propelled towards nozzle 112

However, there are certain limitation to this type of rack and pinion gear mechanism; notably that the speed of repeated bursts of droplets is limited by the speed of the mechanism, and attempts to operate the device more rapidly may result in the rack and pinion gear mechanism wearing prematurely or jamming. Therefore, a different type of mechanism to drive the air for forming droplets is desired. The present invention utilizes a semi-free rotating crankshaft actuator that offers the desired improved functionality for the device. Although the piston can move freely forward by the spring force, the connection with the drive train is never lost. The moment the piston needs to be pulled back, the drive train also ensures that the piston stroke is completed first.

Figure 3A:
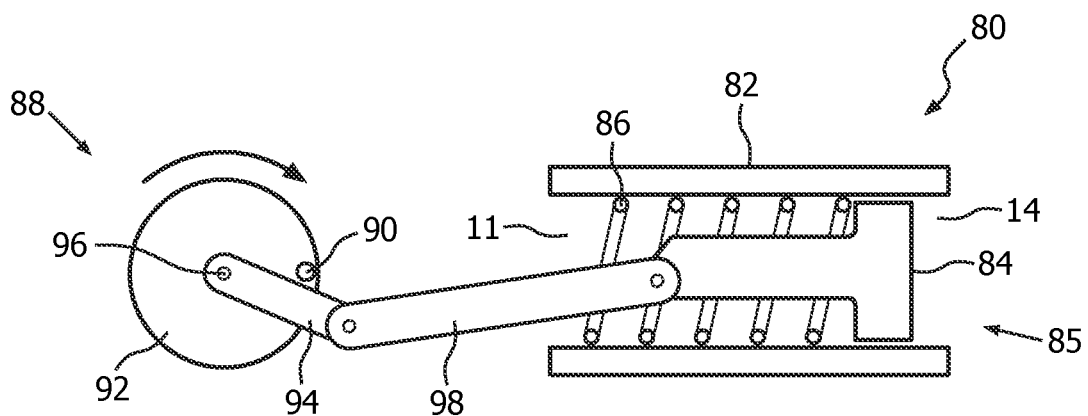

With reference now to FIG. 3A, a schematic diagram view is shown illustrating various components of a semi-free rotating crankshaft actuator 80 that includes a cylinder or chamber 82, a spring loadable plunger 84 with spring 86, and a crank-rod mechanism 88, to pre-stress and fast release a spring loadable plunger for an oral healthcare appliance according to an embodiment of the present disclosure. The semi-free rotating crankshaft actuator 80 includes a combination of a crank-rod mechanism 88 with the spring loadable plunger 84 (or spring loaded piston) having a driving pin 90 or peg on a driving gear or wheel 92. The driving pin 90 forces a semi-freely rotatable crank shaft 94 about a driving axis 96, the crank shaft 94 being coupled to the plunger 84, via a connection rod 98, for pushing the plunger 84 forward to it intended position in case the plunger gets stuck in the forward moving phase, as will be discussed further herein with reference to FIG. 4. As shown in FIG. 3A, the driving pin 90 couples with the driving gear 92 and the semi-freely rotatable crank shaft 94. The semi-freely rotatable crank shaft 94 is mounted co-axially on the driving axis 96 of the driving gear 92 and it can rotate independently from the driving gear 92 (i.e., it is freely rotatable about the driving axis and semi-freely rotatable about the driving axis in view of the driving pin).

Figure 3B:
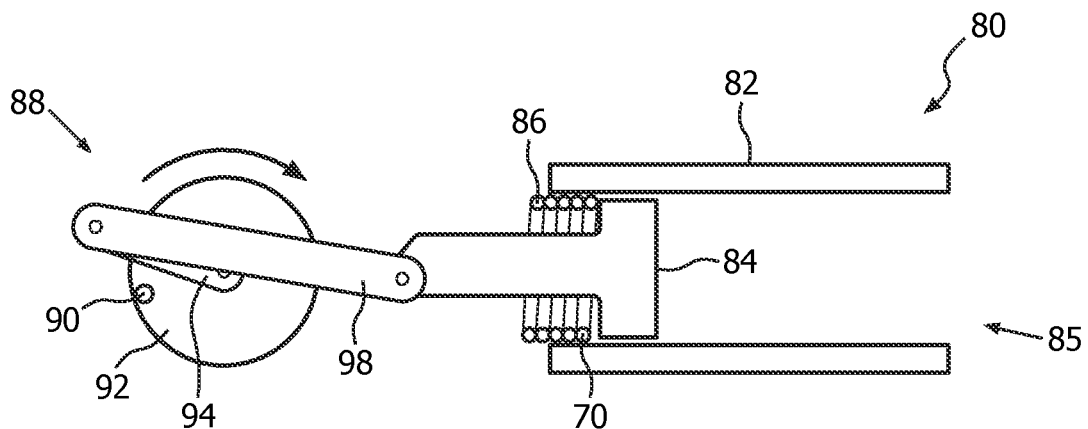
Figure 3C:
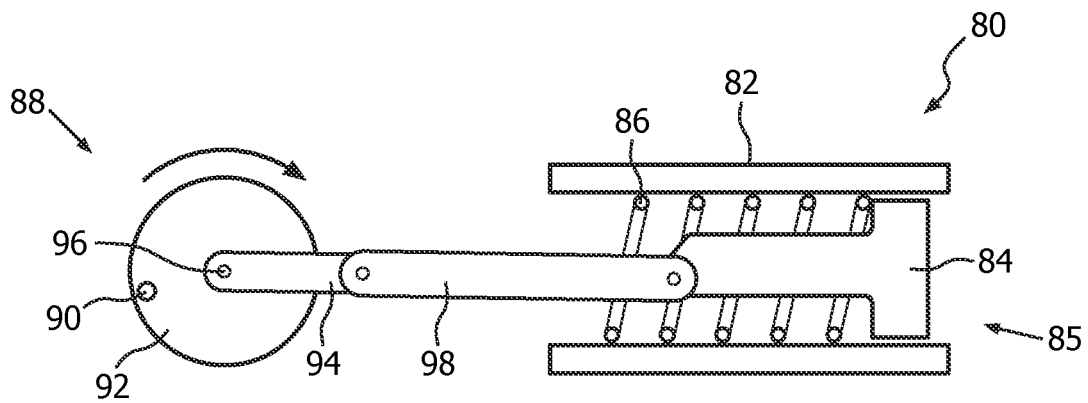

Referring now to FIGS. 3A, 3B, and 3C, there are shown several schematic diagram views illustrating various stages of intended drive train operation of the semi-free rotating crankshaft actuator for an oral healthcare appliance. In FIG. 3A, for compressing and/or loading the spring 86, the plunger 84 is pulled via the driving gear 92 rotating the driving pin 90, which engages and pushes the crank shaft 94. In FIG. 3B, with continued rotation of the driving gear 92, the driving pin 90 pushes the crank shaft 94 to just beyond a top dead center position of the crank shaft 94, whereupon the spring 86 becomes released and takes over driving the crank shaft 94, via a pulling force. In addition, the crank shaft 94 pulls away from and loses contact with the driving pin 90. The plunger 84 is also moved by release of the spring 86, further being moved at a velocity faster than that when being moved in the opposite direction by the crank shaft 94. In FIG. 3C, if no blocking of the plunger 84 occurs, then the spring 86 drives the plunger 84 to its desired end position as shown in the figure. Thereafter, the cycle repeats again as discussed with reference to FIGS. 3A and 3B herein above.

Figure 4:
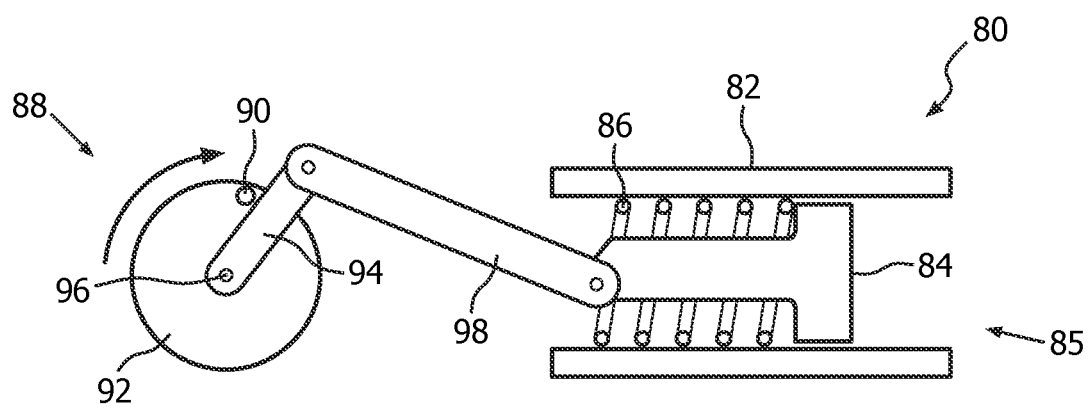

With reference now to FIG. 4, a schematic diagram view is shown illustrating an example of an intended drive train operation of the semi-free rotating crankshaft actuator configured for overcoming an abnormal or unintended condition of the drive train plunger during operation of the actuator of FIGS. 3A-3C, the abnormal or unintended condition arising in response to a force, acting on the plunger against the spring direction, which can vary, for example, due to friction of the plunger seal and/or an obstruction of the output nozzle and/or other causes. As discussed herein with reference to FIG. 3B, when the driving pin 90 pushes the crank shaft 94 to just beyond a top dead center position of the crank shaft 94, the spring 86 becomes released and takes over driving the crank shaft 94, via a pulling force. In addition, the crank shaft 94 pulls away from and loses contact with the driving pin 90. The plunger 84 is also moved by release of the spring 86. If the plunger 84 is blocked before the plunger reaches its desired end position, then the continued rotation of the drive wheel 92 causes the drive pin 90 to catch up to and drive the crank shaft 94, via a pushing force, which drives the plunger 84 to its desired end position. Thereafter, the cycle repeats by compressing the spring 86 again, as discussed with reference to FIGS. 3A and 3B herein above. Similarly, a situation may occur where subsequent to the spring being released, the plunger is moved to the desired end position, and then bounces back, getting stuck at an undesired end position that occurs subsequent to the desired end position, but before the tensioned position. In the later instance, the continued rotation of the drive wheel 92 causes the drive pin 90 to catch up to and drive the crank shaft 94, via a pushing force, which drives the plunger 84 from the undesired end position to the tensioned position.

The embodiments discussed herein provide various advantages. For example, as the crankshaft 94 of the crank mechanism 88 can freely move forward by the spring 86 once released, high forward piston velocities can be realized resulting in high pressure buildup and high spray/jet velocities. In addition, physical contact between the piston or plunger 84 and the crank mechanism 88 drive train is never lost so the embodiments of the present disclosure advantageously overcome and do not suffer from a mismatch between components of the drive train during spring compression. Furthermore, with the presence of the driving pin 90, no locking issue can occur as the piston or plunger 84 moves forward, as described herein.

With reference now to FIGS. 5 and 6, cut-away perspective view is shown taken along the principal axis of the actuator 80 according to one embodiment of the present disclosure.

Figure 8:
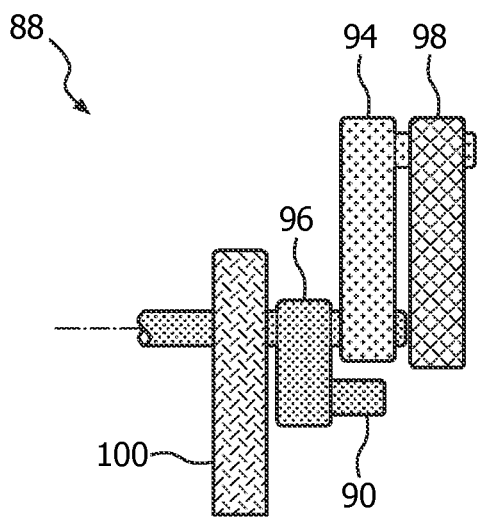
FIG. 8 is a schematic diagram view of the various components of the semi-free rotating crankshaft actuator, taken along line 8-8 of FIG. 7, according to an embodiment of the present disclosure.

With reference now to FIG. 7, a schematic diagram view is shown illustrating various components of a semi-free rotating crankshaft actuator 80 to pre-stress and fast release a spring loadable plunger 84 for an oral healthcare appliance according to another embodiment of the present disclosure. A pin 90 is fixed, via a driving member 192, to an axis 96 which is driven by an external torque (not shown). The axis 96 is supported via framing or housing member 100. Crank 94 is mounted to axis 96, so that crank 94 can rotate freely around axis 96. The rotation of axis 96 and crank 94 will be coupled in the case where crank 94 moves slower than the axis 96, and pin 90 engages and then drives the crank 94. The crank mechanism further drives a connection rod 98, which is attached to plunger 84. The plunger 84 moves within the cylinder 82, and is pushed towards its outer position by spring 86. FIG. 8 shows a schematic diagram view of the various components of the semi-free rotating crankshaft actuator, taken along line 8-8 of FIG. 7.

Referring now to FIGS. 9A, 9B, and 9C, there are shown schematic diagram views illustrating various stages of intended drive train operation of the semi-free rotating crankshaft actuator 80 for an oral healthcare appliance of FIG. 7. In FIG. 9A, for compressing and/or loading the spring 86, the plunger 84 is pulled via the driving member 192 rotating the driving pin 90, which engages and pushes the crank shaft 94. In FIG. 9B, with continued rotation of the driving member 192, the driving pin 90 pushes the crank shaft 94 to just beyond a top dead center position of the crank shaft 94, whereupon the spring 86 becomes released and takes over driving the crank shaft 94, via a pulling force. In addition, the crank shaft 94 pulls away from and loses contact with the driving pin 90. The plunger 84 is also moved by release of the spring 86, further being moved at a velocity faster than that when being moved in the opposite direction by the crank shaft 94. In FIG. 9C, if no blocking of the plunger 84 occurs, then the spring 86 drives the plunger 84 to its desired end position as shown in the figure.

Thereafter, the cycle repeats again as discussed with reference to FIGS. 9A and 9B herein above.

With reference now to FIG. 10, a schematic diagram view is shown illustrating an example of an intended drive train operation of the semi-free rotating crankshaft actuator 80 configured for overcoming an abnormal or unintended condition of the drive train plunger during operation of the actuator of FIG. 9, the abnormal or unintended condition arising in response to a force, acting on the plunger against the spring direction, which can vary due to friction of the plunger seal or an obstruction of the output nozzle. As discussed herein with reference to FIG. 9B, when the driving pin 90 pushes the crank shaft 94 to just beyond a top dead center position of the crank shaft 94, the spring 86 becomes released and takes over driving the crank shaft 94, via a pulling force. In addition, the crank shaft 94 pulls away from and loses contact with the driving pin 90. The plunger 84 is also moved by release of the spring 86. If the plunger 84 is blocked before the plunger reaches its desired end position, then the continued rotation of the driving member 192 causes the drive pin 90 to catch up to and drive the crank shaft 94, via a pushing force, which drives the plunger 84 to its desired end position. Thereafter, the cycle repeats by compressing the spring 86 again, as discussed with reference to FIGS. 9A and 9B herein above. Similarly, a situation may occur where subsequent to the spring being released, the plunger is moved to the desired end position, and then bounces back, getting stuck at an undesired end position that occurs subsequent to the desired end position, but before the tensioned position. In the later instance, the continued rotation of the driving member 192 causes the drive pin 90 to catch up to and drive the crank shaft 94, via a pushing force, which drives the plunger 84 from the undesired end position to the tensioned position.

Referring now FIG. 10, there is shown an exploded schematic view of a crank mechanism 88 that comprises a drive pin and crankshaft arrangement of a semi-free rotating crankshaft actuator for an oral healthcare appliance according to another embodiment of the present disclosure. The embodiment of FIG. 10 is similar to the embodiments previously discussed herein, with the following differences. The driving axis 96 and the crank 94 are coupled via a one way coupling. The one way coupling includes a pin 190 and one-way clutch 191 (i.e., one-directional clutch) that uses, for example, a spring tightly wound around an axis, and having desired spring characteristics as may be required for a given crank mechanism and semi-free rotating crankshaft actuator implementation. The pin 190 is fixedly attached to the driven circular drive gear 92 of the crank mechanism 88. In other words, the drive pin rotatably driven about the drive axis 96 comprises a driven circular drive gear 92 having a principal surface, a one-way clutch 191 having a first end thereof affixed to a pin 190 that extends perpendicular from the principal surface located on the circular drive gear at a given radial distance from the drive axis, and wherein a second end of the one-way clutch 191 is configured for one-directional driving engagement with the crank shaft 94. FIG. 12 shows a schematic view of the crank mechanism 88 for the semi-free rotating crankshaft actuator of FIG. 11.

The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. A semi-free rotating crankshaft actuator for an oral healthcare appliance, comprising:
    a chamber having a principal axis, an interior surface with a spring compression stop at a proximal end thereof and an outlet at a distal end thereof;
    a spring loadable plunger operable within the chamber along the principal axis between a tensioned position near the proximal end of the chamber and a released position near the distal end of the chamber, wherein the spring loadable plunger comprises a plunger having a distal end thereof configured for traversing the interior surface of the chamber along the principal axis in a fluid tight relationship and (ii) a spring, positioned over a proximal end of the plunger and positioned between the compression stop and the distal end of the plunger, having at least two compression states including a first compression state greater than a second compression state, wherein responsive to the spring being unloaded from the first compression state to the second compression state, the spring actuates the plunger at a first velocity from the tensioned position to the released position, wherein the released position comprises an end position within the chamber in response to a first actuator condition; and
    a crank mechanism coupled to the spring loadable plunger for cycling the spring loadable plunger between the tensioned and released positions, wherein the crank mechanism comprises at least a drive pin rotatably driven about a drive axis, and a crank shaft semi-freely rotatable about the drive axis, wherein the crank shaft couples to the spring loadable plunger and is partially driven about the drive axis via
        (i) the drive pin in a first operational mode that comprises loading the spring into the first compression state in response to the crank shaft pulling the plunger from a desired end position to the tensioned position; and
        (ii) the spring loadable plunger in a second operational mode that comprises actuating the plunger from the tensioned position to the released position in response to the spring being unloaded from the first compression state to the second compression state.

2. The semi-free rotating crankshaft actuator according to claim 1, wherein the first operational mode further comprises the plunger being initially located at the desired end position within the chamber and the drive pin engaging the crank shaft for exerting a pushing force on the crank shaft, causing the crank shaft coupled to the spring loadable plunger to move the spring loadable plunger at a second velocity from the released position to the tensioned position, the second velocity being less than the first velocity.

3. The semi-free rotating crankshaft actuator according to claim 2, wherein the second velocity comprises a velocity sufficient for maintaining a desired duty cycle for loading and unloading of the spring, further for inputting and subsequently expelling a desired quantity of air and/or liquid.

4. The semi-free rotating crankshaft actuator according to claim 1, wherein the second operational mode further comprises the plunger being initially located at the tensioned position within the chamber and the drive pin losing engagement with the crank shaft in response to the spring of the spring loadable plunger (a) actuating the plunger at the first velocity from the tensioned position to the released position and (b) exerting a pulling force on the crank shaft.

5. The semi-free rotating crankshaft actuator according to claim 1, wherein a third operational mode further comprises the plunger initially coming to rest at an undesired end position within the chamber prior to reaching the desired end position and the drive pin engaging the crank shaft for exerting a pushing force on the crank shaft, causing the crank shaft coupled to the spring loadable plunger to move the spring loadable plunger at the second velocity from the undesired end position to the desired end position, and then further on to the tensioned position.

6. The semi-free rotating crankshaft actuator according to claim 1, wherein the crank mechanism further comprises a connection member coupled between the crank shaft and the spring loadable plunger.

7. The semi-free rotating crankshaft actuator according to claim 6, wherein a first end of the connection member is rotatably coupled to a distal end of the crank shaft and a second end of the connection member is rotatably coupled to a proximal end of the plunger.

8. The semi-free rotating crankshaft actuator according to claim 1, wherein the drive pin rotatably driven about the drive axis comprises a circular drive gear having a principal surface, the drive pin further being extended perpendicular from the principal surface and located on the circular drive gear at a given radial distance from the drive axis.

9. The semi-free rotating crankshaft actuator according to claim 1, wherein the drive pin rotatably driven about the drive axis comprises a drive lever crank having a principal surface, the drive pin further being extended perpendicular from the principal surface and located on the drive lever crank at a given distance from the drive axis.

10. The semi-free rotating crankshaft actuator according to claim 1, wherein the drive pin rotatably driven about the drive axis comprises a driven circular drive gear having a principal surface, a one-way clutch having a first end thereof affixed to a pin that extends perpendicular from the principal surface located on the circular drive gear at a given radial distance from the drive axis, and wherein a second end of the one-way clutch is configured for one-directional driving engagement with the crank shaft.

11. An oral healthcare appliance, comprising:
    the semi-free rotating crankshaft actuator according to claim 1, wherein the outlet at the distal end of the chamber is configured for receiving a nozzle having a guidance tip;
    at least one reservoir for receiving at least one of a liquid and a gas;
    a motor operable for driving the drive axis of the semi-free rotating crankshaft actuator and delivering at least one of a liquid and a gas from the at least one reservoir to the chamber; and
    a controller for controlling operation of the motor.

12. A method of providing semi-free rotating crankshaft actuation for an oral healthcare appliance, comprising:
    providing a chamber having a principal axis, an interior surface with a spring compression stop at a proximal end thereof, and at least one outlet at a distal end thereof;
    operating a spring loadable plunger within the chamber along the principal axis between a tensioned position near the proximal end of the chamber and a released position near the distal end of the chamber, wherein the spring loadable plunger comprises (i) a plunger having a distal end thereof configured for traversing the interior surface of the chamber along the principal axis in a fluid tight relationship and (ii) a spring, positioned over a proximal end of the plunger and positioned between the compression stop and the distal end of the plunger, having at least two compression states including a first compression state greater than a second compression state, wherein responsive to the spring being unloaded from the first compression state to the second compression state, the spring actuates the plunger at a first velocity from the tensioned position to the released position, wherein the released position comprises (a) a desired end position within the chamber in response to a first actuator condition and (b) an undesired end position within the chamber, different from the desired end position, in response to a second actuator condition, different from the first actuator condition; and cycling, via a crank mechanism, the spring loadable plunger between the tensioned and released positions, wherein the crank mechanism comprises at least a drive pin rotatably driven about a drive axis, and a crank shaft semi-freely rotatable about the drive axis, wherein the crank shaft couples to the spring loadable plunger and is partially driven about the drive axis via (i) the drive pin in a first operational mode that comprises loading the spring into the first compression state in response to the crank shaft pulling the plunger from the desired end position to the tensioned position, and (ii) the spring loadable plunger in a second operational mode that comprises actuating the plunger from the tensioned position to the released position in response to the spring being unloaded from the first compression state to the second compression state.

13. The method of claim 12, wherein the first velocity comprises a velocity sufficient for developing at least a minimum required pressure within the chamber for expelling, a desired quantity of air and/or liquid, and/or mixture of air and liquid.

14. The method of claim 12, wherein the first operational mode further comprises the plunger being initially located at the desired end position within the chamber and the drive pin engaging the crank shaft for exerting a pushing force on the crank shaft, causing the crank shaft coupled to the spring loadable plunger to move the spring loadable plunger at a second velocity from the released position to the tensioned position, the second velocity being less than the first velocity, wherein the second operational mode further comprises the plunger being initially located at the tensioned position within the chamber and the drive pin losing engagement with the crank shaft in response to the spring of the spring loadable plunger (a) actuating the plunger at the first velocity from the tensioned position to the released position and (b) exerting a pulling force on the crank shaft, and wherein a third operational mode further comprises the plunger initially coming to rest at the undesired end position within the chamber prior to reaching the desired end position and the drive pin engaging the crank shaft for exerting a pushing force on the crank shaft, causing the crank shaft coupled to the spring loadable plunger to move the spring loadable plunger at the second velocity from the undesired end position to the desired end position, and then further on to the tensioned position.

15. The method of claim 14, wherein the second velocity comprises a velocity sufficient for maintaining a desired duty cycle for loading and unloading of the spring, further for inputting and subsequently expelling a desired quantity of air and/or liquid, and/or mixture of air and liquid.

* * * * *